United States Patent [19]

Nichols

[11] 3,985,298

[45] Oct. 12, 1976

[54] CONTROLLED RELEASE MATERIALS AND METHOD OF USE

[75] Inventor: Larry D. Nichols, Arlington, Mass.

[73] Assignee: Moleculon Research Corporation, Cambridge, Mass.

[22] Filed: Nov. 1, 1974

[21] Appl. No.: 519,812

Related U.S. Application Data

[63] Continuation-in-part of Ser. No. 518,797, Oct. 29, 1974, which is a continuation-in-part of Ser. No. 363,267, May 23, 1973, Pat. No. 3,846,404.

[52] U.S. Cl. .................................. 239/54; 426/3; 427/212; 427/214; 427/439; 428/304; 428/403

[51] Int. Cl.$^2$ .......................................... A61L 9/04

[58] Field of Search ............... 239/53, 54; 260/223, 260/230; 426/3; 427/212, 214, 244, 336, 402, 439; 428/304, 403

[56] References Cited

UNITED STATES PATENTS

| | | | |
|---|---|---|---|
| 2,238,476 | 4/1941 | Monteith | 239/53 |
| 3,261,746 | 7/1966 | Copley | 239/54 |
| 3,423,491 | 1/1969 | McLain | 264/49 |
| 3,557,083 | 1/1971 | Sacco | 260/230 |
| 3,567,118 | 3/1971 | Shepherd | 239/54 |
| 3,688,985 | 9/1972 | Engel | 239/54 |
| 3,769,066 | 10/1973 | Maierson | 427/336 |
| 3,795,533 | 3/1974 | Gauri | 427/336 |
| 3,857,964 | 12/1974 | Yolles | 426/3 |

FOREIGN PATENTS OR APPLICATIONS

| | | | |
|---|---|---|---|
| 652,079 | 11/1962 | Canada | 426/3 |
| 964,569 | 7/1964 | United Kingdom | 427/244 |

*Primary Examiner*—Michael R. Lusignan
*Assistant Examiner*—Dennis C. Konopacki
*Attorney, Agent, or Firm*—Richard P. Crowley

[57] ABSTRACT

A process for the controlled release of a substance which comprises impregnating a substance to be released into and within a cellulosic polymer-liquid composite material as a part of or all of the liquid phase, and the controlled release material as produced.

20 Claims, No Drawings

CONTROLLED RELEASE MATERIALS AND METHOD OF USE

REFERENCE TO PRIOR APPLICATIONS

This application is a continuation-in-part of application Ser. No. 518,797, filed Oct. 29, 1974, which application is a continuation-in-part of application Ser. No. 363,267, filed May 23, 1973 now U.S. Pat. No. 3,846,404, issued Nov. 5, 1974, both applications incorporated by reference herein.

BACKGROUND OF THE INVENTION

Many commercial products contain components which exercise a beneficial effect for only a limited time after introduction into their intended environment, being rapidly consumed, metabolized, vaporized or otherwise lost. To have continued effectiveness, such products must be reapplied at intervals, providing an undesirable and perhaps harmful excess at the times of reapplication and barely adequate levels at later times.

Microencapsulation techniques address the problem of controlled release by enclosing the transient component within hollow shells of differing size and wall thickness, which dissolve or otherwise rupture at different intervals to provide a more or less steady supply.

The temporary shells of microencapsulation can be replaced by more permanent semipermeable shells which allow escape through the shell wall without shell destruction, or the entire microcapsule replaced by a homogeneous semipermeable vehicle containing the active ingredient as a pure impregnant, solute or precipitate. In this latter process, the host vehicle serves not to enclose the active ingredient within a wall, but as a carrier from which it can only slowly escape by solution, diffusion, evaporation or some other rate-limited process. The utility of a particular host material as such a carrier depends on such properties as liquid content, pore size, compatibility with various environments, surface energy and wettability, susceptibility to post-impregnation modifications in properties, and ease of manufacture in suitable physical forms. The commercial exploitation of slow release carrier vehicles requires the availability of inert, microporous materials which are readily impregnable with a wide variety of substances, have controllable porosity, and possess acceptable physical properties.

SUMMARY OF THE INVENTION

My invention relates to the process of employing polymer-liquid composite materials prepared from organic or inorganic cellulose esters as vehicles for the controlled release of active materials into an intended environment, and to the controlled release materials so employed. I have found that my polymer-liquid composite (PLC) materials may contain from over 99% to less than 70% liquid; e.g., to 60% and, as prepared in accordance with my prior teachings, are transparent, coherent materials readily formed as films, fibers or microspheres, and, as I have discovered further, possess in unique degree properties required for their use as ultramicroporous vehicles for controlled release applications.

Properly selected PLC materials, as described and defined in my previous patent applications, are not harmed by most common liquids and solutions, maintaining their integrity and liquid-to-solid ratio in the presence of such fluids as alcohols, ethers, aliphatic and aromatic hydrocarbons, ketones and esters containing four or more carbon atoms, water, and aqueous solutions with a pH from 2 to 11. PLC materials are prepared so as to possess interconnected internal pores as large as a few hundred Angstroms; e.g., 250 Angstroms, or as small as a few Angstroms; e.g., 10 Angstroms; e.g., 1 to 250 Angstroms. I have found that the initial porosity can be permanently readjusted to smaller pore size, either before or after incorporation of the desired impregnant, by controlled removal of a portion of the internal liquid phase; for example, by evaporation. PLC materials readily exchange their internal liquid for other miscible liquids or solutions, and thus allow pressurized or diffusive permeation of liquid through their structure, support solute diffusion within their liquid phase at rates comparable with polymer-free solvents, and serve as media for common reactions and precipitations much in the manner of pure liquids, except for rate limitations imposed by the absence of nondiffusive mixing.

PLC materials containing a component which is to be released at a controlled rate may possess oleophilic, hydrophobic surfaces, even when composed largely of water, and thus can be incorporated into release-retarding gums and oils from which hydrophilic, oleophobic vehicles would readily be expelled by surface forces. Inclusion of active ingredients in PLC vehicles as sparingly soluble particles, or as precipitates formed by solvent exchange or chemical reaction in situ, provide an internal reservoir which maintains a constant concentration of the active ingredient in solution inside the PLC vehicle. Combined with normal diffusive release, this property of PLC materials provides so-called zero-order release in which a nearly uniform level of active ingredient is maintained throughout the active life of the vehicle.

I have found that the use of PLC materials permits retarding the evaporative release of volatile materials not only through diffusive effects and control of effective surface area, but also through an actual depression in the vapor pressure of the contained volatile substance. Evaporation of a liquid from a PLC material causes irreversible shrinkage of the material, a process which consumes energy much like crushing an inelastic sponge. This additional energy requirement is superimposed on the normal heat of vaporization of the volatile material, leading to a higher effective heat of vaporization and a lower effective vapor pressure. Crushing of the material is mediated by surface tension forces at the surface of the material, placing the internal liquid at a high negative pressure, and the Gibbs equation can thus be used to calculate the induced lowering of vapor pressure.

The release rates achieved by PLC materials containing material to be released can be further modified by various auxiliary methods. The PLC vehicle, itself, can be modified; for example, by skinning or other modification of its external surface layer. The solvent phase, if any, can be modified; for example, by addition of cosolutes or nonsolvent liquids. Finally, the immediate external environment can be altered; for example, by coating the PLC vehicle with a liquid which wets the PLC material and impedes escape of the active ingredient, or by the addition of a release-promoting agent to the external medium.

My invention is directed to controlled release materials and to a process for controlling the duration and rate of release of transitory substances into some environment where they exercise a desired function, which process comprises: impregnating of the substance or a precursor into an ultramicroporous polymer-liquid composite material having as its distinct and interpenetrating phases an organic or inorganic cellulose ester and a liquid solvent for the impregnant, the impregnation being performed by contact of the desired substance or precursor, in pure form or in solution, with said polymer-liquid composite material at a temperature and for a time sufficient to allow complete diffusive exchange between the initial internal liquid and the impregnant liquid; isolating of the impregnated polymer-liquid composite material, hereafter termed the vehicle, optionally with removal of excess intersticial liquids; optional treating of the impregnated vehicle with a reagent or precipitant capable of converting the initial impregnant into a desired final form, and/or modification of the impregnated vehicle by complete or partial removal of its internal liquid phase without loss of the desired impregnant; optional enveloping of the vehicle with a barrier film or coating of a poor or nonsolvent for the impregnant; and incorporating of the completed vehicle into a medium suitable for application in the desired environment as a controlled release material.

My process includes the initial impregnating liquid containing additives or cosolutes capable of modifying the release rate of the impregnant in its final form.

The PLC material used includes cellulose esters like cellulose triacetate or cellulose nitrate, or a discrete or molecular mixture thereof.

The PLC material may be in film, fiber or microspherical form; e.g., having a particle size of 1 to 500 microns; e.g., 50 to 300 microns.

In the process, the impregnation temperature is typically less than 35°C; e.g., 20° to 30°C, and the time of contact is one minute or more; e.g., 1 to 30 minutes.

The isolation step may be conducted by sieving, filtering or centrifugation.

The removal of intersticial liquid in the process may be accomplished by sorption into another porous medium, and the removal of the internal liquid phase may be accomplished by evaporation or annealing.

The envelopment of the vehicle may be accomplished by exposure to a poor or nonsolvent liquid which wets the vehible externally, or the envelopment of the vehicle may be accomplished by exposure to a liquid or vapor which superficially coalesces the polymer-liquid composite material of the vehicle into a less permeable, denser form.

The controlled release material may be contained as an incorporated component in an aerosol propellant, a food product, a chewing gum, a pharmaceutical compound, an agricultural product, or a cosmetic preparation.

The desired function of my material and process may comprise a flavoring, scent, coloring, medication, dermatological action, pesticidal action, or agricultural fertilizer.

My process of using cellulosic polymer-liquid composite material as a controlled release vehicle, the method of preparing such controlled release-containing materials and the controlled release materials themselves will be described for the purpose of illustration only by the following examples directed to some, but not all, materials, applications, methods of preparation and uses of my invention.

EXAMPLE 1

Small segments of 9 mil thick PLC film containing 15% cellulose triacetate and 85% water were floated on a 0.5% solution of zinc chloride and small droplets of a 5% solution of sodium fluorescein placed on the exposed upper surface. Within 30 seconds, a visible precipitate of yellow zinc fluorescein began to form below each droplet within the film. After 20 minutes, the films were carefully lifted from the lower solution and immediately rinsed with flowing water for 15 seconds. Each zinc fluorescein inclusion was then punched out at the center of a 1 cm disk of film. The inclusions could be seen to be associated with a slight swelling of the film at the location of the precipitated dye. Prolonged extractions of the sparingly soluble zinc fluorescein with cell stirred, room temperature water showed total loadings of about 0.5 mg at each site, with a nearly constant release rate of 7.6 micrograms per minute for the first 30 minutes of extraction. The remaining zinc fluorescein dissolved out more slowly, with extraction being complete in about 4 hours as shown by the disappearance of the precipitated dye and the loss of ability to dye fresh water. Pure zinc fluorescein is between 0.1% and 0.2% soluble in water, and a 0.5 mg sample in pure form dissolves in an adequate volume of stirred water in less than one minute.

EXAMPLE 2

A drop of lemon oil was allowed to sorb into a small bed of silica gel, a medium known to extend the lifetime of this and many other fragrances. A similar quantity of lemon oil was impregnated into PLC microspheres containing 8% cellulose triacetate and 92% water after first replacing the water with ethyl alcohol to provide miscibility with the essential oil. Ambient exposure of both samples indicated an odor lifetime of about 2 days, with pronounced drift in the character of the odor from the silica gel and no perceptible drift in the case of the impregnated sample, indicating that the POROPLASTIC vehicle, unlike the silica gel, possesses little, if any, reactivity or preferential retention. (POROPLASTIC is a registered trademark of Moleculon Research Corporation for polymer-liquid composite material).

EXAMPLE 3

An aqueous suspension of PLC microspheres, ranging in diameter from about 74 to 149 microns and composed of 15% cellulose triacetate and 85% water, was spun down on a centrifuge. The supernatant water was decanted off and replaced with ethyl alcohol, and the microspheres resuspended by shaking. Again the microspheres were spun down, and this rinsing with fresh ethyl alcohol repeated three times, on each occasion using a volume of added alcohol about four times that of the bed of microspheres. This entire process was then repeated using, in place of alcohol, a 20% solution of musk ambrette, a common perfume fixitive, in pure isobutyl isobutyrate, a highly volatile essential oil. The final bed of impregnated microspheres was removed from the centrifuge tube and freed of intersticial liquid by standing on absorbent paper in a closed container to avoid evaporation. A sample of these microspheres calculated to contain 5 mg of isobutyl isobutyrate was then spread evenly over the bottom of a small glass vial about 1.5 cm in diameter and a stream of air flowing at 80 ml/minute passed through the vial and into a thermal conductivity gas analysis detector.

Similar experiments were performed with the omission of the musk ambrette, and with isobutyl isobutyrate, with and without musk ambrette, on a bed of talc. In all cases, the evolution of isobutyl isobutyrate vapor from the samples showed a sharp initial rise followed by a smooth inverse exponential decline, the data yielding good straight lines on semilog paper. The data can thus be represented by values of the single parameter of half-life for each experiment, the half-life being the time required for loss of half of the isobutyl isobutyrate present. On talc, with or without musk ambrette, the half-life was 1.6 minutes. In the PLC microspheres, the half-life without musk ambrette was 2.8 minutes, and with musk ambrette 5.9 minutes, for prolongation factors of 1.75 and 3.69, respectively. Similar runs using silica gel in place of talc yielded samples with a definite and unpleasant shift in odor, and air-flow analyses indicating partial decomposition of the ester.

EXAMPLE 4

An aqueous suspension of PLC microspheres containing 85% water and 15% cellulose triacetate was spun down on a centrifuge and the supernatant water decanted off. A solution of ten parts per million of the dye Brilliant Green was added, in volume equal to about four times the volume of the microsphere bed, and the spheres resuspended by shaking. The spheres were again spun down, revealing that all of the color attributable to the dye had passed into the microspheres. Subsequent exposure of the dyed microspheres to pure water gave no indication of dye release, but storage of the dyed microspheres together with undyed spheres separately in the same container of water showed that perceptible coloration passed from the dyed to undyed sample in a period of two weeks, indicating a small but real equilibrium dye concentration in the external aqueous phase. Addition of 0.01% of a cationic agent, such as a quaternary ammonium wetting agent, to a suspension of the dyed spheres gave perceptible dye release into the external aqueous phase in a period of minutes, and wetting agent concentrations in excess of 1% produced very rapid dye release. Neutral and anionic wetting agents gave no perceptible release.

EXAMPLE 5

0.9 mg pure aluminum chlorhydrate powder placed in 100 ml of stirred water dissolves entirely within 1 minute as shown by electrical conductivity of the solution. A 2.7 mil film of POROPLASTIC PLC material containing 30% cellulose triacetate and 70% of a 1:1 water:ethyl alcohol mixture was impregnated with a 5% solution of aluminum chlorhydrate in the same solvent mixture and dried. Samples containing about 0.2 mg of aluminum chlorhydrate placed in 100 ml of stirred water showed a constant release of solute for more than 2 hours, with a calculated prolongation factor of about 180. The same film impregnated with aluminum chlorhydrate as a 5% solution in pure water, without ethyl alcohol, delivered its contained solute over a period of 45 minutes.

EXAMPLE 6

Impregnation of PLC microspheres containing 8% cellulose triacetate and 92% water with a 40% solution of a sweetening agent, such as sodium saccharine, was followed by drying in air overnight and grinding of the resulting material to a fine powder. This powder was blended into a typical chewing gum bolus at a concentration calculated to provide 0.1% sodium saccharine in the final product. A board of organolepticians judged the resulting gum to develop maximum sweetness in about 7 minutes, with sweetening persisting for 40 minutes. This is to be compared with standard saccharinated gums containing no controlled release agent, which lose their sweetness in 4 to 5 minutes.

EXAMPLE 7

An experiment similar to that of Example 6 was conducted with PLC microspheres rinsed with ethyl alcohol and then impregnated with pure peppermint oil. The resulting product was blended into chewing gum bolus at a level calculated to provide 0.33% of peppermint oil. Flavor lifetime was judged to be in excess of 30 minutes, compared with a 4- to 5-minute lifetime for gum made with 1% free peppermint oil.

EXAMPLE 8

A light cologne with a normal persistence of 5 to 6 minutes was tested after impregnation into PLC microspheres containing cellulose triacetate and the remainder (a) 70% ethyl alcohol; (b) 85% ethyl alcohol; and (c) 92% ethyl alcohol. Under standard test conditions, the resulting specimens showed fragment lifetimes of 470, 150 and 20 minutes, respectively, with almost no drift in the quality of the fragrance. A similar set of experiments with a fine perfume with a free lifetime of 30 minutes gave extensions to 1400, 520 and 140 minutes. Thus one finds prolongation factors for the 70%-liquid vehicles of 50 to 90, for the 85%-liquid vehicles of 20–30, and for the 92%-liquid vehicles of 4–5, again showing the greater effectiveness of the finer pores in the lower liquid content material at retarding escape of impregnant.

EXAMPLE 9

A vehicle comprising microspheres of composition 15% cellulose nitrate with degree of substitution greater than 2, and 85% water, is impregnated by immersion in an excess of a solution of 10% disodium orthophosphate in water. The resulting impregnated vehicle is freeze-dried to prevent escape of the inorganic salt during dehydration. Admixture of the vehicle preparation with moist soil shows gradual release of phosphate at a rate depending on moisture level, accompanied by slower and more prolonged release of biologically available nitrogen through degradation of the vehicle itself.

EXAMPLE 10

A POROPLASTIC film 20 mils thick, composed of 15% cellulose triacetate and 85% water, was immersed for 1 minute in a 1:1 volume mixture of benzene and methylene chloride, and superficially dried. The presence of the immiscible aqueous phase within the film prevented penetration of the organic liquid into the interior of the film, but the surface character of the film was modified as indicated by increased gloss. When this skinned film was allowed to stand in air along with an untreated, but otherwise identical, piece of film, the rate of initial weight loss due to evaporation of water was found to be 1%/minute for the treated sample and 1/5%/minute for the untreated control. After 1 hour, the control had lost all but about 1% of its full initial water content. A similar level of dryness was reached by the skinned sample only after 90 minutes.

The hydrophobic surface of PLC controlled release vehicles composed of cellulose triacetate or cellulose nitrate is converted into a hydrophilic surface by hydrolysis to cellulose; for example, by exposure to concentrated aqueous ammonia or sodium hydroxide, or by treatment with alcoholic sodium methoxide.

The foregoing examples illustrate the controlled release of materials in general, such as dyes, as well as sweetening and flavoring agents in chewing gum, and fragrances, essential oils, scents and the like in perfume materials and antiperspirant agents. My PLC material may also be employed as controlled release vehicles for pharmaceutical ingredients, such as drugs, antibiotics, anticontraceptive agents such as spermacides and the like.

Various changes, modifications and addition may be made by those skilled in the art to the embodiments described herein without departing from the spirit and scope of my invention.

What I claim is:

1. A process for controlling the duration and rate of release of a material, which process comprises:
   a. providing a polymer-liquid composite material composed of a cellulosic polymer phase and a cellulosic nonsolvent liquid phase, which is a solvent for the material to be impregnated, comprising from about 70 to 99% of the material, the material characterized by being ultramicroporous, with interconnecting pore sizes of from about 10 to about 250 Angstroms and subject to irreversible shrinking on evaporation of the liquid phase;
   b. impregnating the said material with a substance which is desired to be released at a controlled rate and for a desired period of time by contacting the substance with the said material to provide for a diffusive exchange between the liquid phase and the substance, the substance a liquid in pure form or in solution which is miscible with the liquid phase, and which is not a solvent for the polymer, thereby placing the substance within the interior pores of the material, the substance consisting essentially of a pharmaceutical agent, a sweetening agent, an essential oil, a perfume fixative, an antiperspirant, a dye, a dermatological agent, a fragrance, a pesticide or a fertilizer;
   c. recovering the substance-impregnated material; and
   d. incorporating the impregnated material into the environment in which the controlled release is desired, and releasing the impregnated substance from the material.

2. The process of claim 1 wherein the original liquid phase is water or an alcohol.

3. The process of claim 1 wherein the substance is alcohol-soluble and the impregnated material contains the substance in an alcohol-liquid phase.

4. The process of claim 1 which includes the impregnated material in microspherical form having a particle size of from about 1 to 500 microns.

5. The process of claim 1 which includes removing at least part of the liquid phase of the impregnated material without loss of the impregnated substance after recovering and prior to incorporating the material in its environment.

6. The process of claim 1 wherein the cellulosic polymer is cellulose triacetate or cellulose nitrate or a discrete or molecular mixture thereof.

7. The process of claim 1 wherein the temperature of impregnation is 35°C or less.

8. The process of claim 1 which includes, after recovering and prior to incorporating, removing intersticial liquid from the impregnated material by sorption of the liquid into another porous medium.

9. The process of claim 1 which includes after recovering removal of some of the intersticial liquid from the impregnated material by evaporation of the liquid.

10. The process of claim 1 wherein the substance is a sweetening agent or essential oil, the liquid phase is water, the impregnated material is in microspherical form, and which includes incorporating the impregnated microspherical material into a chewing gum bolus to provide prolonged sweetening and flavoring actions.

11. The process of claim 1 wherein the substance is an essential oil or perfume fixative, or combinations thereof, the liquid phase is an alcohol, the impregnated material is in microspherical form, and which includes incorporating the impregnated microspherical material into a material to prolong the scent.

12. The process of claim 1 wherein the impregnated material has an aqueous liquid phase, and which includes treating the external surface of the impregnated material after incorporating the material in the environment with a cationic wetting agent to increase the rate of release of the substance into the environment.

13. The process of claim 1 wherein the composite material is in microspherical form and the nonsolvent liquid phase is an alcohol, and wherein the substance is a solution comprising musk ambrette as a perfume fixative and isobutyrate as an essential oil.

14. The process of claim 1 wherein the composite liquid material is in microspherical form, wherein the liquid phase is alcohol or water or a combination thereof, and the substance is a solution containing aluminum chlorhydrate as an antiperspirant agent.

15. The process of claim 1 wherein the composite material is in microspherical form, the nonsolvent liquid phase is water and the substance is a water solution of sodium saccharine as a sweetening agent.

16. The process of claim 1 wherein the composite material is in microspherical form, and which includes evaporating the liquid phase of the substance-impregnated material to shrink irreversibly the microsphere prior to incorporating the material in the controlled release environment.

17. The process of claim 1 wherein the composite material is in microspherical form, and which includes incorporating the impregnated material containing a sweetening agent, a pharmaceutical agent, an essential oil, or a combination thereof, into a chewing gum bolus.

18. The process of claim 1 wherein the composite material is in microspherical form, and which includes incorporating the impregnated material containing a fragrance or perfume fixative, or a combination thereof, into a cosmetic or perfume formulation.

19. The process of claim 1 which includes coating a film of a liquid material which wets the composite material to impede the release of the impregnated substance.

20. A controlled release polymer-liquid composite material which comprises a cellulosic polymer of cellulose triacetate or cellulose nitrate or a discrete or molecular mixture thereof with a particle size of from about 1 to 500 microns, the polymer characterized by a plurality of ultramicroporous interconnecting pores having a size of from about 10 to 250 Angstroms, and having a liquid phase composed of a nonsolvent comprising alcohol or water or mixtures thereof, which liquid phase comprises from about 70 to 99% of the polymer-liquid composite material, the polymer irreversibly shrunk by evaporation of the liquid phase from its condition prior to diffusion the liquid phase containing a diffused substance therein which is soluble with the alcohol or water, or which is miscible with the liquid phase, and which is not a solvent for the polymer, the substance consisting essentially of a pharmaceutical agent, a sweetening agent, an essential oil, a fixative, an antiperspirant, a dye, a dermatological agent, a fragrance, a pesticide or a fertilizer, which substance, within the liquid phase of the pores, is released over a period of time.

* * * * *